United States Patent [19]

Senum et al.

[11] Patent Number: 5,300,468
[45] Date of Patent: Apr. 5, 1994

[54] CARBONACEOUS ADSORBENT REGENERATION AND HALOCARBON DISPLACEMENT BY HYDROCARBON GASES

[75] Inventors: Gunnar I. Senum; Russell N. Dietz, both of Patchogue, N.Y.

[73] Assignee: Associated Universities, Inc., Washington, D.C.

[21] Appl. No.: 906,946

[22] Filed: Jun. 30, 1992

[51] Int. Cl.$^5$ .................. B01J 20/34; C07C 17/38
[52] U.S. Cl. .................. 502/34; 95/141; 95/148; 570/179
[58] Field of Search .................. 502/34, 56, 31; 570/179; 55/71, 74; 95/141, 148

[56] References Cited

U.S. PATENT DOCUMENTS

| | | | |
|---|---|---|---|
| 3,720,626 | 3/1973 | Benzaria et al. | 210/30 |
| 3,922,217 | 11/1975 | Cohen et al. | 208/299 |
| 4,055,399 | 10/1977 | Parrish | 23/230 |
| 4,256,038 | 3/1981 | Dietz et al. | 102/28 |
| 4,303,411 | 12/1981 | Chen et al. | 23/230 |
| 4,501,324 | 2/1985 | Sandiford et al. | 166/250 |
| 4,520,109 | 5/1985 | Simmonds et al. | 436/56 |
| 4,551,154 | 11/1985 | Malcosky et al. | 48/154 |
| 4,690,689 | 9/1987 | Malcosky et al. | 48/174 |
| 4,709,577 | 12/1987 | Thompson | 422/83 |
| 4,725,551 | 2/1988 | Thompson | 422/70 |
| 4,742,873 | 5/1988 | Craig, III | 166/252 |
| 4,775,475 | 10/1988 | Johnson | 210/634 |
| 4,784,672 | 11/1988 | Sircar | 55/74 |
| 5,087,778 | 2/1992 | Yates | 502/34 |

OTHER PUBLICATIONS

R. N. Dietz, Perfluorocarbon Tracer Technology, in BNL Publication No. 38847, *Regional and Long-Range Transport of Air Pollution*, S. Sandroni, Ed., Elsevier Publishers B.V., Amsterdam, pp. 215-247 (1987).

Senum et al., BNL Publication No. 42769 Informal Report, *Hydrocarbon Precombusting Catalyst Survey and Optimization for Perfluorocarbon Tracer Analysis in Subsurface Tracer Applications*, May 1989.

Senum et al., BNL Publication No. 43811R (DE90000248), *A Perfluorocarbon Tracer Transport and Dispersion Experiment in the North Sea Ekofisk Oil Field*, Jul. 1990.

R. N. Dietz, BNL Publication No. 46265 (Rev. Sep. 1991), *Commercial Applications of Perfluorocarbon Tracer (PFT) Technology*, Jun. 1991.

*Primary Examiner*—Paul E. Konopka
*Attorney, Agent, or Firm*—Margaret C. Bogosian

[57] ABSTRACT

This invention describes a process for regeneration of halocarbon bearing carbonaceous adsorbents through which a carbonaceous adsorbent is contacted with hydrocarbon gases, preferably propane, butane and pentane at near room temperatures and at atmospheric pressure. As the hydrocarbon gases come in contact with the adsorbent, the hydrocarbons displace the halocarbons by physical adsorption. As a result of using this process, the halocarbon concentration and the hydrocarbon eluant is increased thereby allowing for an easier recovery of pure halocarbons. By using the process of this invention, carbonaceous adsorbents can be regenerated by an inexpensive process which also allows for subsequent re-use of the recovered halocarbons.

7 Claims, 8 Drawing Sheets

CARBONACEOUS ADSORBENT REGENERATION AND HALOCARBON DISPLACEMENT BY HYDROCARBON GASES

This invention was made with government support under contract No. DE-AC02-76CH00016, between the U.S. Department of Energy and Associated Universities, Inc. The government has certain rights in the invention.

BACKGROUND OF THE INVENTION

This invention relates to adsorbent regeneration and halocarbon recovery from carbonaceous adsorbents as assisted by hydrocarbon gases. More particularly, this invention relates to a process of regenerating carbonaceous adsorbents bearing trace amounts of halocarbon compounds by purging the adsorbents with hydrocarbon gases such as propane, butane and pentane and the possible recovery of the halocarbon from this hydrocarbon stream.

Carbonaceous adsorbents are used routinely for the adsorption of halocarbons from gaseous and aqueous streams as used in air and water purification processes. After use, these adsorbents are either disposed of or, if economically feasible, are regenerated.

Conventional regeneration processes include thermal processes and solvent extraction processes. During a thermal regeneration process the adsorbent is heated at temperatures up to 450° C. with an inert gas such as nitrogen or air allowing the halocarbons to become physically desorbed from the carbonaceous adsorbent.

During a solvent extraction process, the adsorbent is flushed with a liquid solvent, essentially dissolving the adsorbed halocarbon; the halocarbon can then be recovered from the solvent.

The above conventional processes have many drawbacks. For example, the thermal regeneration process has high energy requirements and is, therefore, expensive. Moreover, many adsorbed halocarbons are thermally labile and frequently decompose at high temperatures, thereby eliminating any potential for subsequent recovery and re-use of the halocarbons.

The solvent extraction process has many steps. After the adsorbent is flushed with a liquid solvent, the halocarbons must be removed from the solvent. This recovery is frequently difficult. In addition, the spent solvent must be disposed of or further treated. As a result, adsorbent regeneration by the solvent extraction process has many steps, which require equipment, manual labor and is, therefore, costly. Moreover, because the regeneration of certain carbonaceous adsorbents has proven cumbersome and expensive, frequently the spent adsorbent has been simply discarded. Accordingly, it would be advantageous to provide an adsorbent regeneration process which eliminates the need for high temperatures or spent solvent disposal and which is, at the same time, economically competitive to the simple disposal of carbonaceous adsorbents.

It is therefore a primary object of this invention to provide a new, cost effective process for regeneration of carbonaceous adsorbents. Another object of this invention is to recover the previously adsorbed halocarbons for subsequent reuse.

SUMMARY OF THE PRESENT INVENTION

The present invention is a process for regeneration of halocarbon bearing adsorbents by which a carbonaceous adsorbent is contacted with hydrocarbon gases such as propane, butane and pentane at temperatures near room temperature and at atmospheric pressure.

The carbonaceous adsorbents used in the present invention can be selected from a non-limiting list consisting of Pittsburgh charcoal, coconut charcoal, granular activated charcoal such as Ambersorb ®, and charcoal manufactured by Applied Science Inc., and a charcoal distributed by the Tigg Corporation.

Prior to regeneration, the adsorbents have been used to adsorb halocarbons from air or in water purification processes. A non limiting list of halocarbons includes perfluoro-methylcyclopentane, perfluoro-methylcyclohexane, perfluoro-1,2 dimethylcyclohexane, perfluoro-1,3 dimethylcyclohexane, perfluoro-1,4 dimethylcyclohexane, perfluorotrimethylcyclohexane, trichlorofluoromethane, dichlorodifluoromethane, dichlorofluoromethane, chlorodifluoromethane and chlorotetrafluoroethane.

In another embodiment, the process of regeneration of the charcoal adsorbents includes passing pure propane or butane gas through the adsorbent charcoal bed at room temperature. The regeneration effect decreases linearly with decreasing propane concentration in nitrogen or air.

Butane was found to be more effective than propane in eluting halocarbons at the same temperature. Consequently, pure butane is thought to be especially effective in eluting the more adsorbed halocarbons. Moreover, the application of moderate temperatures, i.e., from 50° C. to 100° C., increases the rate of halocarbon elution with propane or butane. However, further increases in temperature decreases the rate of halocarbon elution because lesser amounts of propane or butane are being physically adsorbed on the carbonaceous adsorbent at these temperatures.

As a result of the present invention, carbonaceous adsorbents which are presently disposed of in landfills can be regenerated by an inexpensive process which also allows for subsequent reuse of the recovered halocarbons. Because propane or butane gas rapidly elute halocarbons, higher concentrations of halocarbons are found in the propane or butane elution gas. Thus, the halocarbons can be more easily recovered for further re-use. Usually carried out at room temperature, the energy requirements for this process are quite low. Moreover, through the use of this process, the thermal decomposition of thermally sensitive halocarbons is also minimized.

For a better understanding of the present invention, reference is made to the following description and the accompanying drawings. The scope of this invention will be pointed out in the appended claims.

DETAILED DESCRIPTION OF THE INVENTION

In the present invention the halocarbon-bearing carbonaceous adsorbents can be successfully regenerated by eluting the adsorbent with small amounts of hydrocarbon gases. As a result, the halocarbon concentration in the hydrocarbon eluant is increased thereby allowing for an easy recovery of pure halocarbons.

Carbonaceous adsorbents have been widely used in many air and water treatment processes. Ambersorb ®, manufactured by Rohm and Haas, has been used to adsorb chlorocarbons from drinking water supplies. Ambersorb ® is particularly attractive as an adsorbent because of its hydrophobicity which causes it not to swell or clog in the presence of water.

Ambersorb ® has been successfully used as an adsorbent for perfluorocarbon tracers (PFTs), a group of gaseous halocarbons used as tracers in atmospheric dispersion and transportation studies. Because of its hydrophobicity Ambersorb ® has been widely used as a preferred adsorbent in air samplers used for collection of samples which contain perfluorocarbon tracers.

PFTs are detected by using air samplers such as Capillary Adsorption Tube Samplers (CATS) or Brookhaven Atmospheric Tracer Samplers (BATS). In its present configuration a CATS is generally made from glass tubing, ideally having a length of 2.5 inches (6.4mm) and outside diameter of about 6 mm with an inside diameter of 4 mm. The tubing is preferably packed with Ambersorb ® No. 347 e.g., about 64mg for the tubing described above. Sampling occurs either by the process of Fickian diffusion or flowing the sample through the tube. The experimental work leading to this invention was carried on Ambersorb ® bearing CATS. Once adsorbed onto the CATS sampler, the PFT content is analyzed by gas chromatography electron capture detection GC-ECD.

Generally, in a GC-ECD, the constituents in an air sample containing PFTS are thermally desorbed from the CATS and are injected into the GC carrier gas stream via a sample valve. Before entering the chromatographic column all the components are present as a slug. However, the atmosphere contains many compounds whose concentrations exceed those of the adsorbed PFTs and which are also detectable by the electron capture detector (ECD) used to measure the PFTs. These interfering compounds are removed by combustion through a catalyst bed operating at about 200° C. The remaining PFTs are then detected on the GC-ECD.

Virgin granular activated charcoal is another adsorbent which can be regenerated by the process of the invention. Characterized by a very large surface area per unit of volume, activated charcoal can adsorb many gases, liquids or dissolved substances on the surface of its pores. Having excellent physical and chemical stability, activated charcoal is easily produced from readily available materials.

Almost any carbonaceous raw material can be used for the manufacture of activated carbon. Wood, peat, lignite are commonly used for the decolorizing materials. Bone char made by calcining bones is used in large quantity for sugar refining. Nut shells, coconut shells, hardwood, impregnated carbon, coal, petroleum coke, and other residues in either granular, briquette, or pelleted form are used as adsorbent products.

A non-limiting list of activated carbon includes WATERCARB ® as manufactured by Acticarb, Inc., NORIT ®, DARCO ®, HYDRODARCO ®, in powder, granular and extruded forms as manufactured by American Norit Co., SUPER-A ® and powder in granulated carbon forms as manufactured by Anderson Development Co., ACTICARBONE ® and CE-CARBON ® in powder, extruded and granular grades, and CECACARBON ® from Ceca Division of Atochem Inc., powders and formed grades of activated carbon from DeGussa Corp., HICOSORB ® S-502 and S-402 from the Graver Corp./Graver Chemical Division, KATACOL ®, NUCHAR ® in granular and powder grades as manufactured by Westvaco Corp., NIXTOX ®, CANSORB ® and ENVIRON SORB ® in granular activated carbons as manufactured by the Tigg Corporation, activated carbon from Cameron-Yakima, Inc., activated carbon by General Carbon Corp. and other activated carbons as listed in the American Chemical Society Chemcyclopedia, 1988.

Halogenated hydrocarbons or halocarbons are hydrocarbons which include one or more halogens. Perfluorocarbons are halocarbons containing fluorine. Perfluorocarbon tracers (PFTs) are a class of fully fluorinated alkyl substituted cyclohexanes which are uniquely detectable at extremely low levels, down to $10^{-16}$ moles PFT/liter. Chemically stable, non toxic and environmentally safe, highly sensitive for detection and economical, perfluorocarbons have been widely used as tracers in many atmospheric, hydrological and subsurface applications. A non-limiting list of PFTs is given in Table 1.

TABLE 1

| IDENTIFICATION OF PFT COMPONENTS | | |
|---|---|---|
| No. | Symbol | Name(perfluoro-) |
| 1 | PDCB | dimethylcyclobutane |
| 2 | PMCP | methylcyclopentane |
| 3 | PMCH | methylcyclohexane |
| 4 | ocPDCH | ortho$^a$(cis)$^b$-DCH$^c$ |
| 5 | mtPDCH | meta(trans)-DCH |
| 6 | pcPDCH | para(cis)-DCH |
| 7 | PECH | ethylcyclohexane |
| 8 | otPDCH | ortho(trans)-DCH |
| 9 | mcPDCH | meta(cis)-DCH |
| 10 | ptPDCH | para(trans)-DCH |
| 11 | 1 PI | 1-indane |
| 12 | 2 PI | 2-indane |
| 13 | 1 pTCH | 1-trimethylcyclohexane |
| 14 | 2 PTCH | 2-trimethylcyclohexane |

$^a$ortho, meta, and para mean the 1,2-, 1-3-, and 1,4-isomers.
$^b$cis and trans mean the alkyl groups (e.g., methyl) are on the same or opposite sides, respectively, of the molecular plane.
$^c$DCH represents dimethylcylohexane.

Table 2 shows some of the physical properties of PFTs.

TABLE 2

| | PHYSICAL PROPERTIES OF PFTs | | | | |
|---|---|---|---|---|---|
| | Melting | Boiling | Densities | Critical Properties | |
| Abbreviation | Point (°C.) | Point (°C.) | at 20° C. (gm/cc) | $T_c$ (°C.) | $P_c$ (atm) |
| PDCB | −40 | 44.5 | 1.67 | 170.1 | 21.0 |
| PMCP | −45 | 48 | 1.72 | 177.9 | 22.5 |
| PMCH | −39 | 76 | 1.80 | 210.2 | 21.1 |

TABLE 2-continued

PHYSICAL PROPERTIES OF PFTs

| Abbreviation | Melting Point (°C.) | Boiling Point (°C.) | Densities at 20° C. (gm/cc) | Critical Properties $T_c$ (°C.) | $P_c$ (atm) |
|---|---|---|---|---|---|
| o-PDCH[1] | −22 | 102.6 | 1.87 | 235.5 | 18.7 |
| m-PDCH[1] |  | 102.1 | 1.86 |  |  |
| p-PDCH[1] | −70 | 100.9 | 1.85 |  |  |
| PECH | −60 | 101.0 | 1.77 | 234.1 | 18.7 |
| PFI[1] | −8 to −15 | 117.8 | 1.89 | — | — |
| PTCH | −56 | 125.2 | 1.90 | 257.5 | 17.2 |

[1]Exists as cis/trans isomers.

Chlorofluorocarbons, also known as Freons ®, are another class of halocarbons which can be successfully recovered from carbonaceous adsorbents by using the process of the invention. Many chlorofluorocarbons are used as refrigerants in air conditioning units, households or industrial refrigerators and freezers. Additionally, many chlorofluorocarbons can be used as blowing agents, fire extinguishing agents, cleaning fluids and solvents.

A non-limiting list of the Freons ® which can be recovered using the method of the invention includes Freon ® 11, Freon ® 12, Freon ® 21 and Freon ® 22. HCFC 124, or 2-chloro-1,1,1,2-tetrafluoroethane as manufactured by Allied Signal Corporation has also been recovered by the method of invention.

Hydrocarbon gases such as propane, butane, pentane and their isomers or, to a lesser extent, natural gas containing small percentages of these hydrocarbons have been used to elute the halocarbons from the carbonaceous adsorber. The natural gas used in the process of the invention was obtained from an oil field in Bartlesville, Oklahoma. It contained 3% ethane, 1.8% propane, 1% isobutane, 1% n-butane, 0.3% isopentane and 0.3% n-pentane.

An important aspect of this invention is the use of natural gas with the minor constituents of natural gas such as the propanes, butanes, and pentanes, to elute the adsorbed halocarbons from the carbonaceous adsorbent, thereby not only regenerating the adsorbent but also permitting the recovery of the halocarbon for subsequent reuse.

The halocarbons are adsorbed on the carbonaceous adsorbent by physical adsorption. As the hydrocarbon gases come in contact with the adsorbent the hydrocarbons displace the halocarbons by physical adsorption. It has been found that the greater the affinity of the hydrocarbon for adsorption on the carbonaceous adsorbent the better it elutes the halocarbon off the adsorbent. Accordingly, pure methane which has little adsorption capacity onto the adsorbent was not as effective as pure propane, butane or pentane. Pure butane was more effective than propane in regenerating the carbonaceous adsorbent. Bartlesville natural gas, a reference natural gas, proved to be an effective eluent due to the effect of the trace amounts of the minor hydrocarbons such as ethane, propane, isobutane, n-butane, isopentane and pentane present in it.

EXAMPLES

The following Examples are given to illustrate the various features of the invention. The full scope of the invention is defined in the claims which follow the specification.

EXAMPLE 1

One CATS sampler which was previously analyzed to verify the absence of any residual adsorbed PFTs had 1 picoliter ($10^{-12}$ 1/1 Nitrogen) of PFT adsorbed on its charcoal bed. Bartlesville hydrocarbon gas, a reference natural gas was passed entirely through this initial CATS at room temperature and at a flow rate 6.6 cc/min. by placing the PFT adsorbed end of the CATS at the gas flow entrance. The output of the initial CATS was mixed with 13.3 cc/min. of oxygen and combusted in the presence of a vanadium oxide catalyst at 500° C. The effluent from this combustion was then captured on another CATS at 5 minute intervals. These conditions were chosen to ensure the stoichiometric combustion of substantially all of the hydrocarbon which could affect the adsorption of the PFTs onto this collection CATS.

Figure 1:
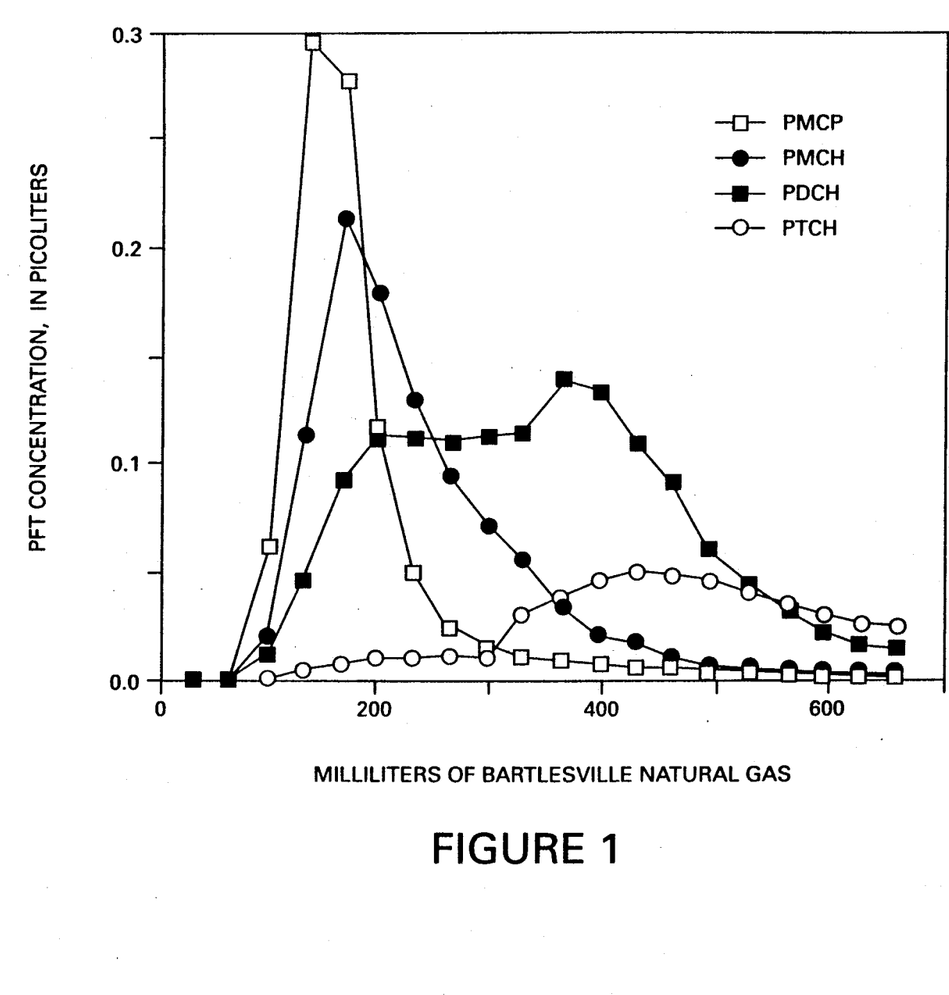
FIG. 1 is a GC-ECD analysis of PFTs eluted from CATS by hydrocarbon gas at room temperature.

The results are shown in FIG. 1. It has been found that at room temperature PFTs have been eluted with small volumes of the hydrocarbon gas. The breakthrough volumes i.e., the amount of natural gas needed to elute 50% of the adsorbed PFTs have been calculated as follows:

| Tracer | Breakthrough Volume. ml At 25° C., CATS |
|---|---|
| PMCP | 24 |
| PMCH | 30 |
| PDCH | 70 |
| PTCH | 84 |

These results can be compared to the same experiment performed with air as the eluting gas. For example, at 25° C. the breakthrough volume for PMCH is about 9000 liters, or approximately 5 orders of magnitude greater. Indeed, the temperature has to be raised to 400° C. for air to elute the PFT with the same efficiency as natural gas at 25° C.

The total concentration of PFTS on the initial and collection CATS was in mass balance. What was initially adsorbed on the initial CATS was 100% recovered on the sum of the collection CATS.

EXAMPLE 2

Figure 2:
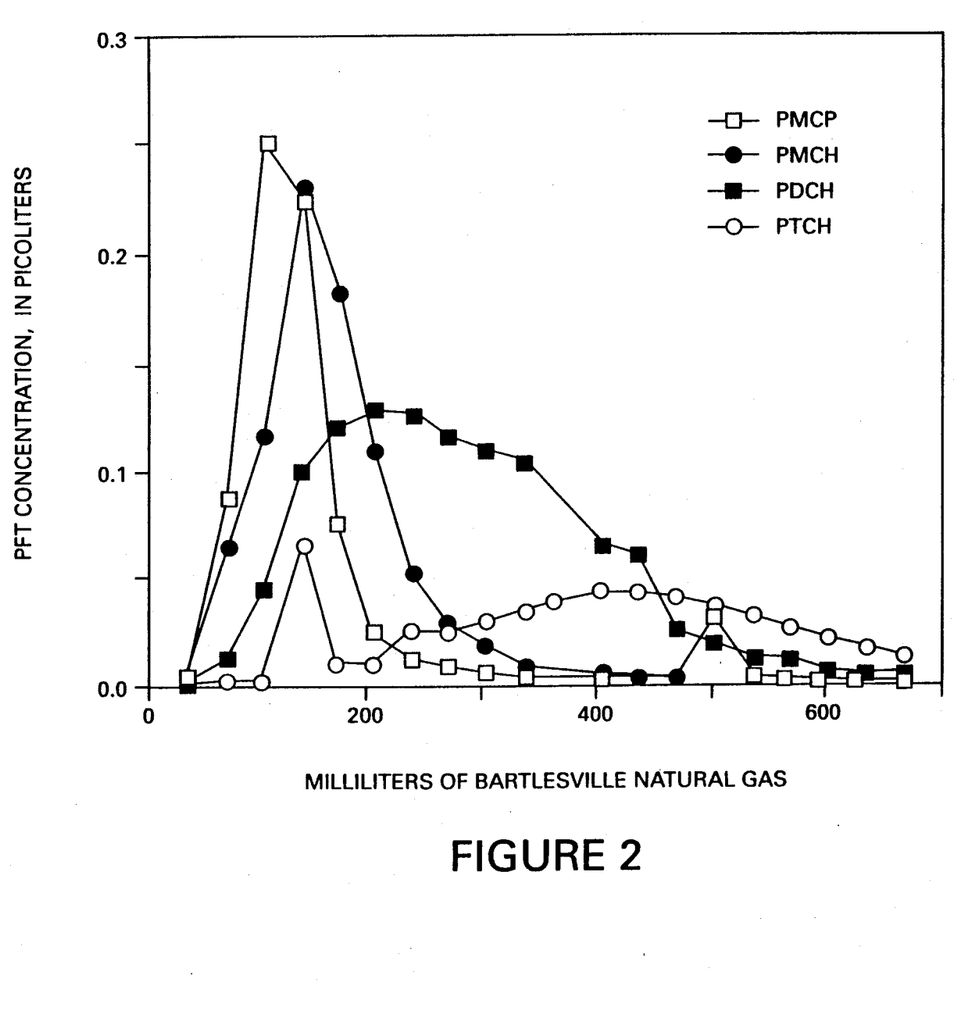
FIG. 2 is a GC-ECD analysis of PFTs eluted from CATS by hydrocarbon 0° C.

The protocol followed in the experiment of Example 1 was repeated except that the initial CATS with the adsorbed PFT was maintained in an ice water bath with an initial coil of tubing, as used to equilibrate the incoming Bartlesville gas at 0° C. The results are shown in FIG. 2. As in the previous example mass balance was achieved. The breakthrough volume were as follows:

| Tracer | Breakthrough Volume, ML At 0° C., Cats |
|---|---|
| PMCP | 17 |
| PMCH | 24 |
| PDCH | 40 |

These results, namely decreasing elution volumes, indicate that the hydrocarbon gas is increasingly physically adsorbing onto the Ambersorb ® surfaces at lower temperature thereby displacing the previously adsorbed PFTs more efficiently and causing the PFTs to elute into the gaseous stream.

EXAMPLE 3

In this example, the initial CATS used had been utilized previously and in many experiments. The CATS was considered to be essentially clean because it had undergone three cleanings by thermal regeneration and had shown no residual PFTs by analysis. A picoliter of PFT standard was adsorbed onto the initial CATS and the CATS was eluted with Bartlesville hydrocarbon gas at 100° C. As in the previous examples, twenty collection CATS were sampled every five minutes for the output of the catalytically combusted gas.

The collection CATS were then analyzed in the Brookhaven Laboratory PFT GC-ECD Analysis System. Initially, and as expected, 1,2-PDCH was detected in the first four secondary CATS. However, in the fifth secondary CATS 1,3-PDCH was observed. The total amount of 1,3-PDCH from the fifth collection CATS and the elution CATS is summarized below:

|                        | mt-PDCH    | mc-PDCH    |
|------------------------|------------|------------|
| Secondary CATS (#5-20) | 363.97 pl  | 343.79 pl  |
| Secondary CATS, #1941  | 181.64 pl  | 185.91 pl  |
| Total                  | 545.61 pl  | 529.70 pl  |

Figure 3:
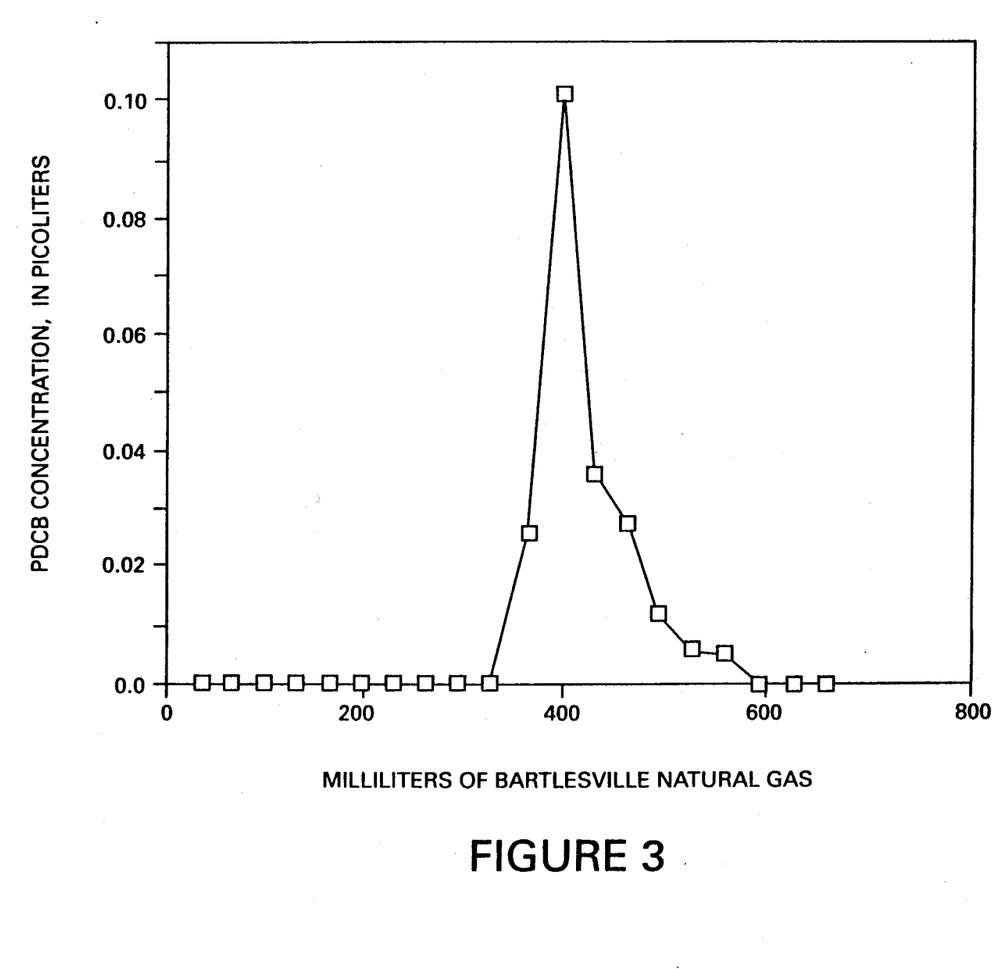
FIG. 3 is a GC-ECD analysis showing the elution of PDCB from CATS by hydrocarbon gas.

Therefore a total of more than a nanoliter of been eluted from this apparently clean CATS. PDCB (not present with PFT standard) was also eluted as shown in FIG. 3.

A total of 0.214 pl of PDCB was eluted. It is important to note that PDCB had not been used as a tracer in any of the experiments.

These results illustrate that small amounts of hydrocarbon gas can release adsorbed PFT from CATS which have been extensively used but were certified as "clean" (by analyses) after repeated thermal regenerations.

These results also show that the thermal regeneration of the adsorbent in the CATS was inadequate. The adsorbent, however, has been effectively regenerated with small amounts of hydrocarbons at much lower temperatures than those required for thermal regeneration.

EXAMPLE 4

This experiment was conducted in order to demonstrate that it was the minor hydrocarbon constituents that were the effective eluants. The procedure of example 1 was repeated in this example. The hydrocarbon stream used to flush the adsorbent with was pure propane. The PFTs eluted rapidly from Ambersorb ® at room temperature.

Figure 4:
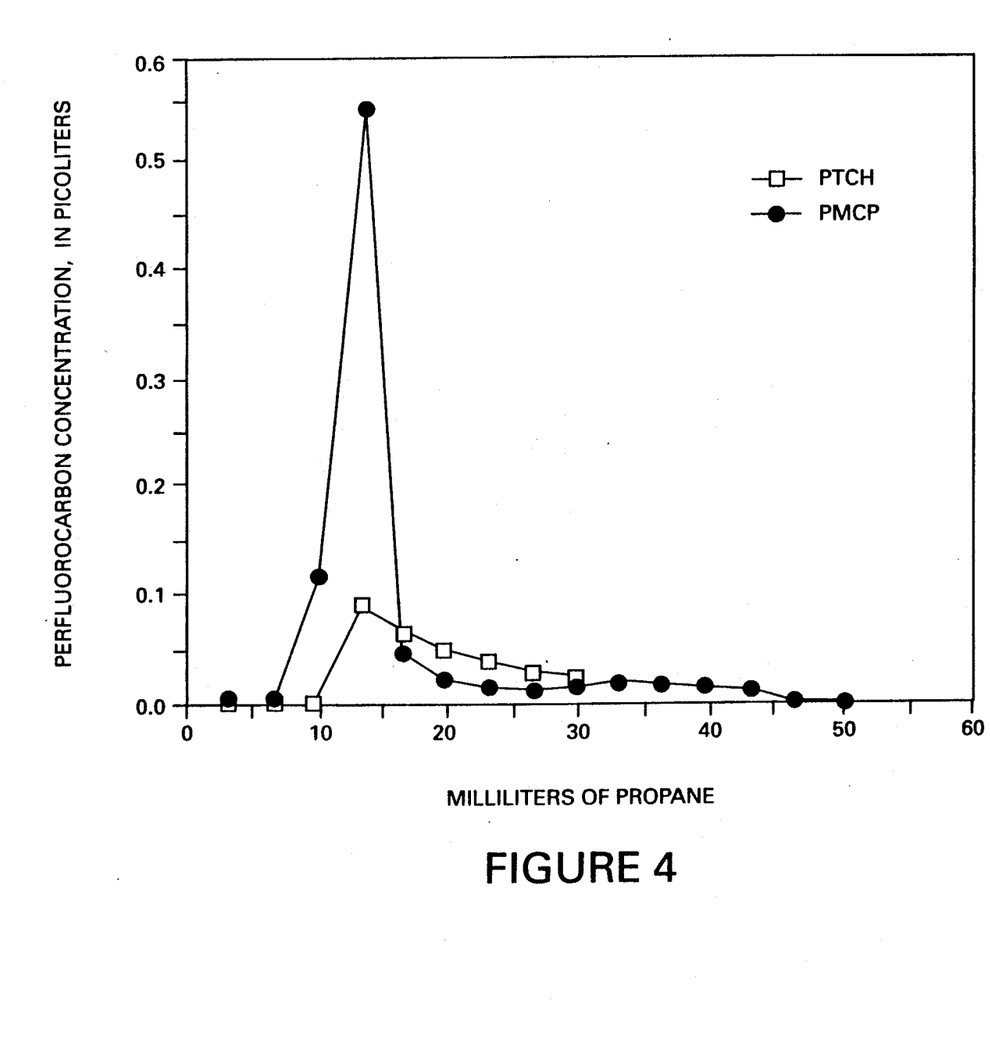
FIG. 4 is a GC-ECD analysis showing elution of PFTs with pure propane gas.

The results are shown in FIG. 4. The elution volume required to elute all of the PFTs was about 14 milliliters of pure propane. This example illustrates that by flushing the adsorbent with small amounts of pure propane gas the PFT is desorbed from the CATS and displaced by the propane gas. This example also shows that propane, which has a greater degree of physical adsorption than pure methane, causes the elution of the halocarbons much more rapidly.

EXAMPLE 5

This experiment examines the effect of flushing propane gas through CATS "certified as clean by analyses."

3.3 cc/min of propane gas was sequentially passed for ten minutes each through a series of twenty initial CATS "certified as clean." The output gas was then stoichiometrically mixed with an amount of oxygen and continuously combusted at 500° C. in a vanadium oxide catalyst bed. The resulting gas and the non-decomposed PFTs were captured on twenty collections CATS. This was done in order to remove all of the propane before recollecting the gas onto the collection CATS.

Out of a batch of twenty intial CATS, three revealed PFTs. The CATS usage history for these three CATS is shown in Table 3.

TABLE 3

| INITIAL CATS HISTORY, PROPANE TREATED CATS |||||||||||||
|--------|----------|--------|--------|--------|--------|--------|--------|--------|--------|--------|--------|-----|
| CAISID | DATE     | PDCB*  | PMCH   | OCPOCH | PIPOCH | MCPOCH | MIPOCH | TPOCH  | PMCP   | U9     | PTCH2  | PIC |
| 9634   | 07/19/90 | 0.0000 | 0.0000 | 0.0000 | 0.0000 | 0.0000 | 0.0000 | 0.0000 | 0.0000 | 0.0000 | 0.0000 | 0   |
| 9634   | 05/05/91 | 0.0000 | 0.0000 | 0.0000 | 0.0000 | 0.0000 | 0.0000 | 0.0000 | 0.0000 | 0.0000 | 0.0000 | 0   |
| 10474  | 07/28/88 | 0.0000 | 0.0000 | 0.0003 | 0.0000 | 0.0000 | 0.0000 | 0.0000 | 0.0000 | 0.0000 | 0.0000 | 0   |
| 10474  | 08/10/88 | 0.0000 | 0.0000 | 0.0004 | 0.0031 | 0.0039 | 0.0056 | 0.0094 | 0.0023 | 0.0000 | 0.0000 | 0   |
| 10474  | 02/24/89 | 0.0000 | 0.0000 | 0.0000 | 0.0000 | 0.0000 | 0.0000 | 0.0000 | 0.0036 | 0.0000 | 0.0000 | 0   |
| 10474  | 10/31/88 | 0.0000 | 0.0049 | 0.0000 | 0.0000 | 0.0000 | 0.0000 | 0.0000 | 0.0000 | 0.0000 | 0.0000 | 0   |
| 10474  | 07/31/90 | 0.0000 | 0.0008 | 0.0003 | 0.0004 | 0.0000 | 0.0002 | 0.0002 | 0.0000 | 0.0000 | 0.0000 | 0   |
| 5682   | 10/06/88 | 0.0000 | 0.2088 | 0.0261 | 0.0947 | 0.0000 | 0.1718 | 0.1784 | 0.0858 | 0.0000 | 0.0000 | 0   |
| 5682   | 04/06/89 | 0.0000 | 0.0132 | 0.0000 | 0.0094 | 0.0000 | 0.0000 | 0.0000 | 0.0015 | 0.0000 | 0.0000 | 0   |
| 5682   | 03/13/90 | 0.0000 | 0.0000 | 0.0000 | 0.0000 | 0.0003 | 0.0000 | 0.0003 | 0.0000 | 0.0000 | 0.0000 | 0   |
| 5682   | 07/02/90 | 0.0000 | 0.0000 | 0.0779 | 0.0000 | 0.1444 | 0.0000 | 0.1500 | 0.0000 | 0.0000 | 0.0000 | 0   |
| 5682   | 02/14/91 | 0.0000 | 0.0008 | 0.0005 | 0.0005 | 0.0016 | 0.0018 | 0.0033 | 0.0000 | 0.0000 | 0.0000 | 0   |
| 5682   | 04/16/91 | 0.0000 | 0.0000 | 0.0000 | 0.0000 | 0.0000 | 0.0000 | 0.0000 | 0.0000 | 0.0000 | 0.0000 | 0   |

*Concentration of tracer in picoliters.

Table 3 indicates the following:

A. CATS #9634 has had two acceptable thermal regenerations or bakechecks, the first in July 1990 and the second in May 1991. No experimental use is noted in its history. Nevertheless, it is possible that these CATS may have been used prior to the establishment of a CATS data base, which provided for the presence of PFT in this sample.

B. CATS #10474 has had an acceptable bakecheck in July 1988, an experimental use in August 1988, and then 3 acceptable bake checks, in October 1988, February 1989, and July 1990 respectively.

C. CATS #5682 has had an acceptable bakecheck in October 1988, a slightly acceptable bakecheck in April 1989, an acceptable bakecheck in March 1990, an experimental use in July 1990, an acceptable bakecheck in February 1990 and April 1991.

The CATS usage history for the three collection CATS are given in Table 4.

TABLE 4

COLLECTION OF CATS. CATS HISTORY

| CAISID | DATE | PDCB* | PMCH | OCPOCH | PIPOCH | MCPOCH | MIPOCH | TPOCH | PMCP | PTCH2 | PIC |
|---|---|---|---|---|---|---|---|---|---|---|---|
| 488 | 09/10/88 | 0.0000 | 0.0052 | 0.0000 | 0.0000 | 0.0019 | 0.0000 | 0.0021 | 0.0059 | 0.0000 | 0 |
| 488 | 11/26/88 | 0.0000 | 0.0024 | 0.0000 | 0.0000 | 0.0000 | 0.0000 | 0.0000 | 0.0028 | 0.0000 | 0 |
| 488 | 08/08/90 | 0.0000 | 1.0175 | 0.5610 | 0.6280 | 0.0000 | 1.2194 | 1.0736 | 0.8890 | 0.0000 | 0 |
| 488 | 11/14/90 | 0.0000 | 0.0000 | 0.0000 | 0.0000 | 0.0009 | 0.0000 | 0.0010 | 0.0000 | 0.0000 | 0 |
| 488 | 04/16/91 | 0.0000 | 0.0000 | 0.0000 | 0.0000 | 0.0000 | 0.0000 | 0.0000 | 0.0000 | 0.0000 | 0 |
| 488 | 05/07/91 | 0.0000 | 0.2861 | 0.2205 | 0.3466 | 0.0000 | 0.8636 | 0.8636 | 0.2030 | 0.0000 | 0 |
| 7776 | 10/08/90 | 0.0000 | 0.0000 | 0.0000 | 0.0000 | 0.0000 | 0.0000 | 0.0000 | 0.0056 | 0.0000 | 0 |
| 7776 | 05/07/91 | 0.0000 | 0.2196 | 0.1426 | 0.1738 | 0.0000 | 0.4648 | 0.4647 | 0.1612 | 0.0000 | 0 |
| 8588 | 02/28/90 | 0.0000 | 0.0000 | 0.0000 | 0.0000 | 0.0000 | 0.0000 | 0.0000 | 0.0000 | 0.0000 | 0 |
| 8588 | 05/01/91 | 0.0063 | 0.0000 | 0.0000 | 0.0000 | 0.0000 | 0.0000 | 0.0000 | 0.0000 | 0.0000 | 0 |
| 8588 | 05/07/91 | 0.0000 | 0.1144 | 0.0702 | 0.1150 | 0.0000 | 0.2584 | 0.2628 | 0.0861 | 0.0000 | 0 |

*Concentration of tracer in picoliters.

The results set forth in Table 4 indicate the following:

A. CATS #488 has had five bakechecks, one unacceptable in August 1990, but two acceptable bakechecks in November 1990 and April 1991.

B. CATS #7776 has had an acceptable bakecheck in October 1990.

C. CATS #8588 has had two acceptable bakechecks in February 1990 and May 1991.

The results from this experiment indicate that propane 10 is releasing PFT from previously certified clean CATS, i.e., propane is more effective at removing residue PFT than nitrogen at 400° C.

EXAMPLE 6

Another experiment was performed to examine the effect of using diluted propane as the eluant gas. A cylinder of 5% propane in nitrogen was prepared. This gas was used to examine the elution of PFT from Ambersorb ®.

One CATS having approximately one picoliter of PFT adsorbed onto the Ambersorb ® bed was used. 15 cc/min of the 5% propane in nitrogen was flown through the CATS. The CATS outlet stream was then mixed with 5 cc/min of oxygen and the resulting stream passed through a vanadium oxide catalyst combuster to remove the propane. The gas was collected onto collection CATS at 5 minute intervals and then analyzed in the PFT ECD-GC Analysis System.

Figure 5:
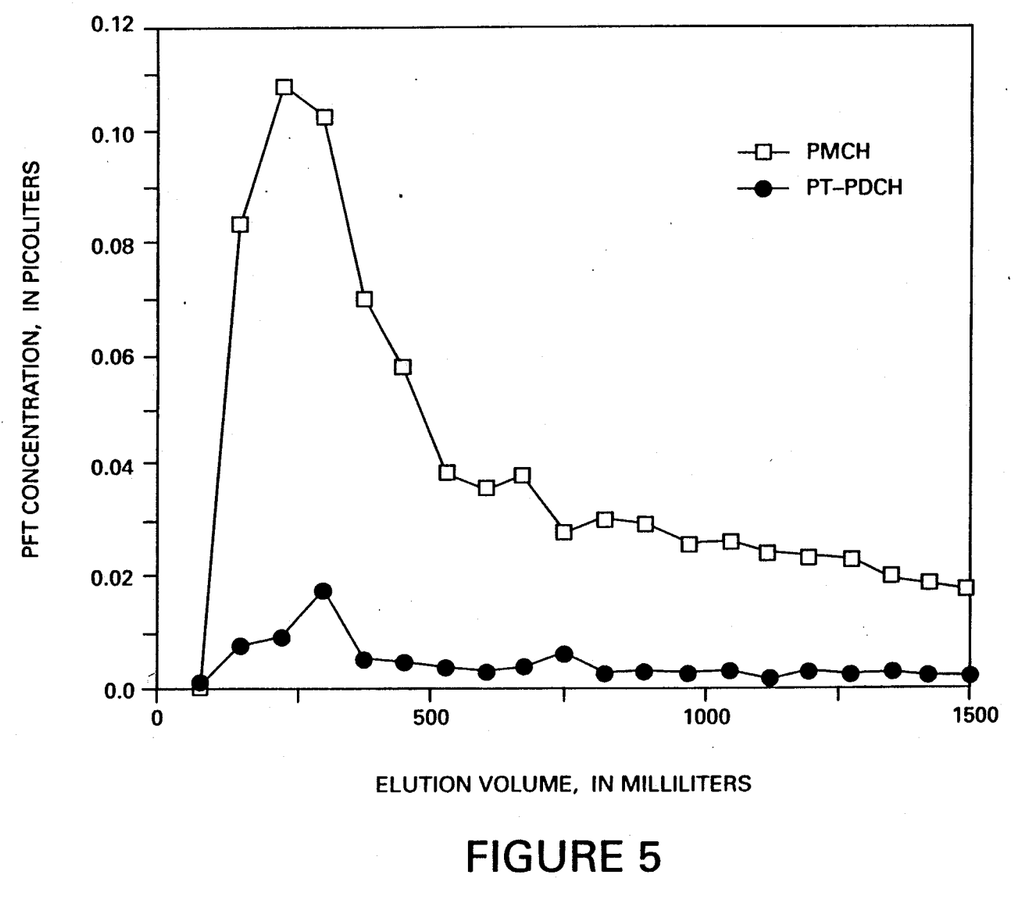
FIG. 5 is a GC-ECD analysis showing elution of PFTs from CATS by 5% propane in nitrogen gas.

The PFT concentration as a function of elution volume is shown in FIG. 5. The elution volume for PMCP was about 225 ml of 5% propane in nitrogen. This is about twenty time the elution volume for PMCP with pure propane as previously measured in Example 4. Consequently, the elution effect varies linearly with the propane concentration. Thus, there are no advantages to using a 5% propane mix since twenty times more gas is needed to perform the same elution as with pure propane. In fact, a closer examination of the elution curve indicates a considerable amount of tailing in the 5% propane mix as compared to the pure propane elution curves. A peak summary sheet for this experiment is shown in Table 5. The total concentration of PMCP on the initial and collection CATS was in mass balance.

TABLE 5

RESIDUAL PFTs REMAINING AFTER ELUTION WITH 5% PROPANE IN NITROGEN GAS PICOLITERS FOR FILE 7392C

| | | PICOLITERS | | | | | | | |
|---|---|---|---|---|---|---|---|---|---|
| SAMPLE | CATSID | PDCB | PMCP | PMCH | ocPOCH | pcPOCH | nPOCHtot | ptPOCH | l2PICH |
| 7392C1 | 3818 | 0.0000 | 0.0000 | 0.0000 | 0.0000 | 0.0000 | 0.0000 | 0.0000 | 0.0000 |
| 7392C2 | 6019 | 0.0000 | 0.0846 | 0.0433 | 0.0078 | 0.0207 | 0.0214 | 0.0090 | 0.0000 |
| 7392C3 | 5921 | 0.0000 | 0.1087 | 0.0537 | 0.0103 | 0.0279 | 0.0289 | 0.0097 | 0.0021 |
| 7392C4 | 9983 | 0.0000 | 0.1031 | 0.0619 | 0.0175 | 0.0501 | 0.0520 | 0.0186 | 0.0058 |
| 7392C5 | 7707 | 0.0000 | 0.0712 | 0.0329 | 0.0061 | 0.0167 | 0.0173 | 0.0058 | 0.0015 |
| 7392C6 | 478 | 0.0000 | 0.0583 | 0.0279 | 0.0056 | 0.0142 | 0.0147 | 0.0052 | 0.0008 |
| 7392C7 | 4131 | 0.0000 | 0.0390 | 0.0234 | 0.0050 | 0.0117 | 0.0122 | 0.0041 | 0.8012 |
| 7392C8 | 8242 | 0.0000 | 0.0365 | 0.0210 | 0.0044 | 0.0106 | 0.0110 | 0.0034 | 0.0000 |
| 7392C9 | 11470 | 0.0000 | 0.0387 | 0.0194 | 0.0010 | 0.0105 | 0.0109 | 0.0045 | 0.0000 |
| 7392C10 | 9768 | 0.0000 | 0.0286 | 0.0195 | 0.0068 | 0.0190 | 0.0197 | 0.0064 | 0.0032 |
| 7392C11 | 3415 | 0.0000 | 0.0308 | 0.0164 | 0.0038 | 0.0095 | 0.0099 | 0.0026 | 0.0000 |
| 7392C12 | 7687 | 0.0000 | 0.0297 | 0.0153 | 0.0032 | 0.0082 | 0.0085 | 0.0029 | 0.0000 |
| 7392C13 | 8981 | 0.0000 | 0.0256 | 0.0161 | 0.0033 | 0.0075 | 0.0078 | 0.0025 | 0.0000 |
| 7392C14 | 2549 | 0.0000 | 0.0258 | 0.0139 | 0.0031 | 0.0083 | 0.0086 | 0.0029 | 0.0000 |
| 7392C15 | 10936 | 0.0000 | 0.0242 | 0.0121 | 0.0028 | 0.0068 | 0.0070 | 0.0017 | 0.0000 |
| 7392C16 | 10109 | 0.0000 | 0.0233 | 0.0117 | 0.0030 | 0.0081 | 0.0084 | 0.0027 | 0.0000 |
| 7392C17 | 6126 | 0.0000 | 0.0222 | 0.0107 | 0.0026 | 0.0071 | 0.0073 | 0.0023 | 0.0000 |
| 7392C18 | 7191 | 0.0000 | 0.0196 | 0.0106 | 0.0028 | 0.0073 | 0.0076 | 0.0025 | 0.0000 |
| 7392C19 | 6926 | 0.0000 | 0.0179 | 0.0093 | 0.0024 | 0.0053 | 0.0055 | 0.0017 | 0.0000 |
| 7392C20 | 7759 | 0.0000 | 0.0177 | 0.0082 | 0.0022 | 0.0054 | 0.0056 | 0.0017 | 0.0000 |
| 7392C21 | 0 | 0.0055 | 0.0000 | 0.0000 | 0.0000 | 0.0000 | 0.0000 | 0.0000 | 0.0000 |
| 7392C22 | 6137 | 0.0000 | 0.1759 | 0.3375 | 0.2253 | 0.7801 | 0.7801 | 0.2728 | 0.2891 |
| TCTR | | 0.900 | 0.900 | 0.900 | 0.900 | 0.900 | 0.900 | 0.900 | 0.900 |

EXAMPLE 7

In this experiment one Ambersorb 347 and one Ambersorb 348 containing CATS were absorbed with one picoliter of PFTs standard. Propane and butane were used to elute the PFTs through Ambersorb ® at room temperature, 90° C. and 137° C. for 30 minutes at a flow rate of 20 cc/min. The results of these experiments given the residual PFT concentrations are shown in tables 6, 7 and 8.

same time. Table 8 illustrates the results of elution with propane or butane at 137° C. In Table 8, the five minute cooling was done only with propane gas.

TABLE 6

Residual PFTS remaining after elution (femtoliters) at room temperature for 30 mintues

|    | CATS # | Conditions   | PMCP | PMCH | oc   | mes  | pt   | pTCH | ML    |
|----|--------|--------------|------|------|------|------|------|------|-------|
|    |        |              |      | PROPANE |   |      |      |      |       |
| 1  | 2743   | Room Temp    | 16-8 | 12.2 | 3.2  | 9.4  | 3.9  | 7.9  | 608   |
| 2  | 2350   | 30 min       | 27.0 | 28.8 | 8.6  | 30.7 | 13.5 | 23.9 | 471   |
| 3  | 2243   | propane      | 23.3 | 28.7 | 11.0 | 35.6 | 15.7 | 21.5 | 648   |
| 4  | 2331   |              | 28.0 | 28.5 | 9.0  | 30.0 | 12.4 | 26.5 | 483   |
| 5  | 9572   |              | 37.3 | 24.4 | 5.4  | 19.1 | 7.2  | 28.3 | 637.8 |
| 6  | 9422   |              | 39.4 | 30.3 | 7.9  | 30.4 | 12.9 | 44.6 | 496.8 |
| 7  | 9808   |              | 46.1 | 32.7 | 6.2  | 24.3 | 10.5 | 30.2 | 612   |
|    |        |              |      | BUTANE |    |      |      |      |       |
| 9  | 2295   | Room Temp    | 26.4 | 14.8 | 8.4  | 23.7 | 10.8 | 1.9  | 608   |
| 10 | 2570   | for 30 min.  | 21.7 | 13.5 | 7.4  | 21.2 | 8.0  | 3.8  | 471   |
| 11 | 2853   |              | 23.3 | 12.7 | 5.0  | 170  | 6.1  | 1.8  | 648   |
| 12 | 2776   |              | 28.6 | 25.3 | 8.2  | 18.7 | 11.9 | 2.5  | 484   |
| 13 | 9000   |              | 23.4 | 15.5 | 5.1  | 12.2 | 4.9  | 0    | 490   |
| 14 | 9852   |              | 29.6 | 18.0 | 6.7  | 17.7 | 6.2  | 1.4  | 637   |
| 15 | 9899   |              | 36.3 | 27.6 | 7.2  | 38.3 | 11.1 | 1.9  | 497   |
| 16 | 9691   |              | 30.1 | 19.1 | 8.3  | 22.4 | 7.9  | 5.5  | 612   |

TABLE 7

Residual PFTS remaining after elution at 90° C. for 30 mintues (femtoliters)

|    | CATS # | Conditions   | PMCP | PMCH | oc   | mes  | pt   | pTCH | ML    |
|----|--------|--------------|------|------|------|------|------|------|-------|
|    |        |              |      | PROPANE |   |      |      |      |       |
| 8  | 2296   | Room Temp    | 7.0  | 7.9  | 2.8  | 23.7 | 3.3  | 17.5 | 608   |
| 9  | 2750   | for 30 min   | 6.8  | 9.5  | 3.9  | 21.2 | 6.4  | 21.7 | 471   |
| 10 | 2853   |              | 6.9  | 8.3  | 3.5  | 17.0 | 3.9  | 19.4 | 648   |
| 11 | 2776   |              | 5.8  | 7.1  | 2.9  | 18.7 | 4.6  | 44.1 | 483   |
| 12 | 9000   |              | 8.2  | 9.9  | 11.3 | 12.2 | 30.6 | 69.4 | 489   |
| 13 | 9852   |              | 10.6 | 9.0  | 7.5  | 17.7 | 12.6 | 37.9 | 637   |
| 14 | 9899   |              | 12.5 | 12.2 | 13.7 | 38.3 | 33.3 | 93.5 | 496   |
| 15 | 9691   |              | 10.2 | 11.1 | 7.4  | 35.4 | 17.1 | 54.9 | 612   |
|    |        |              |      | BUTANE |    |      |      |      |       |
| 1  | 2473   | Room Temp    | 6.0  | 7.3  | 4.1  | 21.8 | 4.4  | 0    | 608.4 |
| 2  | 2350   | for 30 min.  | 2.3  | 2.8  | 0.8  | 15.5 | 3.4  | 0    | 471.3 |
| 3  | 2243   | 5 min.       | 1.9  | 2.0  | 1.6  | 1.2  | 1.3  | 0    | 648   |
| 4  | 2331   | cooling      | 6.2  | 11.0 | 3.3  | 39.9 | 8.5  | 0    | 484   |
| 5  | 9572   |              | 4.4  | 2.3  | 0.2  | 0.6  | 0.8  | 0    | 490   |
| 6  | 9422   |              | 4.0  | 2.3  | 0    | 0.5  | 0    | 0    | 637   |
| 7  | 9808   |              | 5.0  | 1.7  | 0.3  | 0.7  | 1.0  | 0    | 497   |
| 8  | 9638   |              | 6.1  | 2.1  | 1.8  | 0.7  | 0    | 0    | 612   |

TABLE 8

Residual PFTS remaining after elution at 137° C. for 200 mintues (femtoliters)

|    | CATS # | Conditions  | PMCP | PMCH | oc  | mes  | pt   | pTCH | ML    |
|----|--------|-------------|------|------|-----|------|------|------|-------|
|    |        |             |      | PROPANE |  |      |      |      |       |
| 16 | 2641   | 137°        | 1.3  | 1.5  | 1.4 | 1.5  | 1.7  | 12.6 | 608   |
| 17 | 2998   | for 30 min  | 0.9  | 1.1  | 1.7 | 6.3  | 2.6  | 24.7 | 471.3 |
| 18 | 2914   | 5 min.      | 2.0  | 1.7  | 1.9 | 8.2  | 3.7  | 19.2 | 648   |
| 19 | 2407   | cooling     | 1.4  | 1.5  | 1.8 | 7.1  | 3.1  | 22.4 | 483   |
| 20 | 9449   |             | 2.2  | 4.5  | 8.1 | 37.3 | 18.9 | 42.3 | 489   |
| 21 | 9912   |             | 1.4  | 2.7  | 5.6 | 25.7 | 12.1 | 32.3 | 637   |
| 22 | 9577   |             | 1.3  | 4.8  | 8.9 | 42.4 | 20.4 | 46.8 | 496   |
| 23 | 9638   |             | 1.4  | 4.6  | 6.4 | 36.7 | 13.0 | 42.0 | 612   |
|    |        |             |      | BUTANE |   |      |      |      |       |
| 17 | 2641   | 137°        | 10.0 | 0.8  | 1.2 | 0.3  | 0    | 0    | 608   |
| 18 | 2998   | for 30 min. | 0    | 0.3  | 0.2 | 0.9  | 0    | 0    | 471   |
| 19 | 2914   |             | 0    | 0.4  | 0.2 | 0.8  | 1.0  | 0    | 648   |
| 20 | 2407   |             | 0    | 0.7  | 0.3 | 1.1  | 0.5  | 0    | 484   |
| 21 | 9449   |             | 0    | 0    | 0   | 0.4  | 0.2  | 0    | 637   |
| 22 | 9912   |             | 0    | 0    | 0   | 0    | 0    | 0.1  | 497   |
| 23 | 9527   |             | 2.4  | 0.9  | 0.3 | 0.5  | 0    | 0    | 612   |

In Table 7, when butane was used at 90° C., the heat was turned off, and the butane continued to flow for five more minutes of cooling. When propane was used, both the heat and the flow of gas were turned off at the same time. Table 8 illustrates the results of elution with propane or butane at 137° C. In Table 8, the five minute cooling was done only with propane gas.

These results indicated that butane is more effective than propane in eluting PFTs at the same temperature.

Similarly, butane is more effective than propane in eluting PTCH, which is the least volatile or the most adsorbed perfluorocarbon tracer.

EXAMPLE 8

In this example, a CATS was exposed to a flow stream of a PFT standard in Bartlesville natural gas, i.e., 1260 femtoliters of PFT standard per liter of natural gas. A stream of 3.5 cc/min of Bartlesville natural gas was flown through three initial CATS samplers, each packed with a different carbonaceous adsorbent. The three adsorbents used were a charcoal adsorbent as supplied by Applied Science Corp., a coconut charcoal as supplied by Fisher Scientific Company and "Pittsburgh" activated charcoal as supplied by the Pittsburgh Coke and Chemical Corp.

The output from each CATS was mixed with 10.5 cc/min of oxygen and the resulting stream was catalytically combusted using a $V_2O_5$ combustion train. The output from the combustion train was then collected sequentially onto twenty collection CATS at 6 minute intervals.

Figure 6:
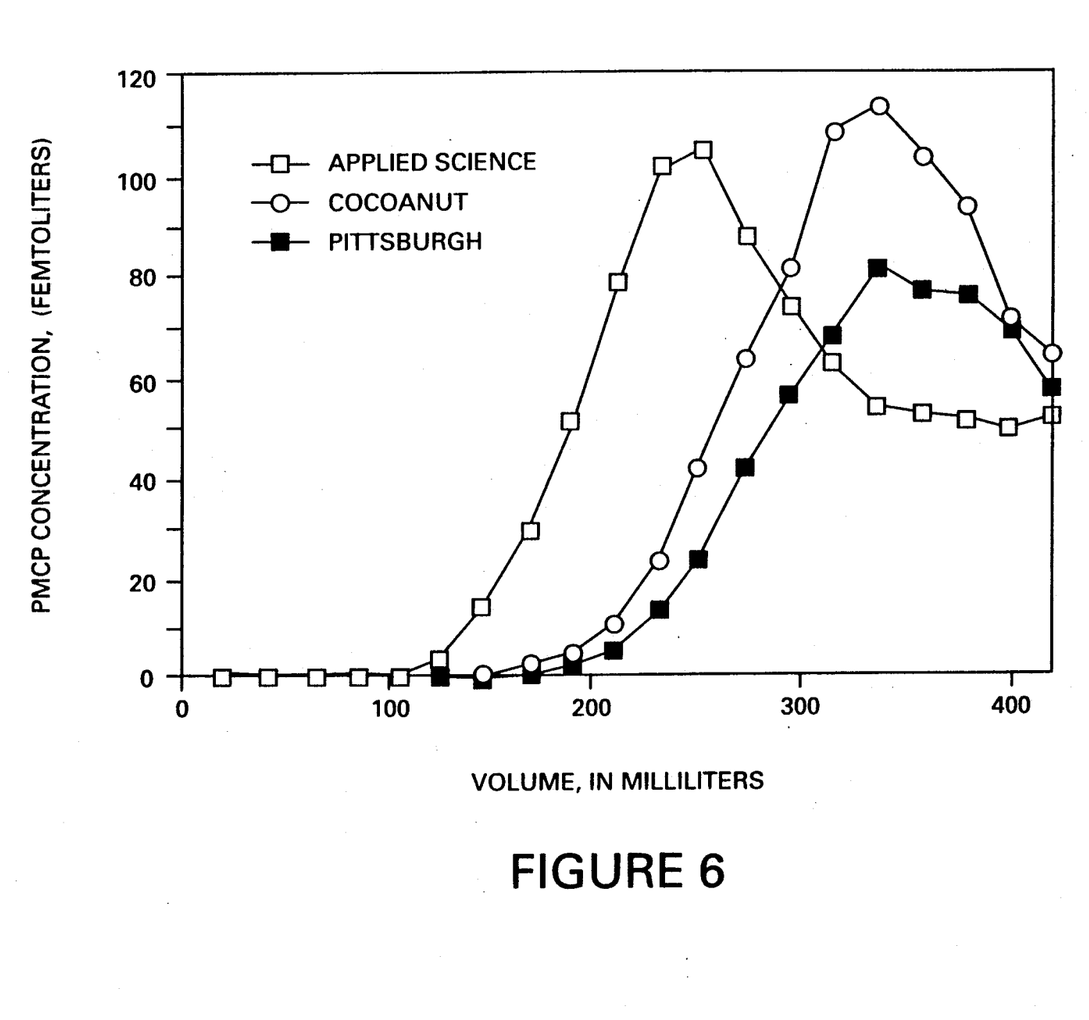
FIG. 6 is a GC-ECD analysis showing the PMCP concentration obtained by elution with Bartlesville natural gas at room temperature as a function of elution volume.

The results are shown in FIG. 6. The effect of eluting PFTs from these three different carbonaceous adsorbents is similar to that shown for Ambersorb® in Example 1. Consequently, the effect of hydrocarbon gases on halocarbon recovery and adsorbent regeneration is universal to all carbonaceous adsorbents.

EXAMPLE 9

The effect of hydrocarbon gases on halocarbon recovery adsorbed onto coconut charcoal. The adsorption isotherm for Freon® 12 on coconut charcoal was experimentally measured at 250° C. The temperature of 250° C. was chosen to allow for the determination of the adsorption isotherm by a standard gas chromatography technique.

A 6 foot × ⅛" O.D. column of coconut charcoal was prepared. This column was then inserted in a Hewlett-Packard 5890A gas chromatograph equipped with a thermal conductivity detector Various quantities of Freon® 12 were injected on this column and were then analyzed by gas chromatography. The adsorption isotherms were calculated by using the relationship that the measured retention volume is equal to the slope of the adsorption isotherm.

Figure 7:
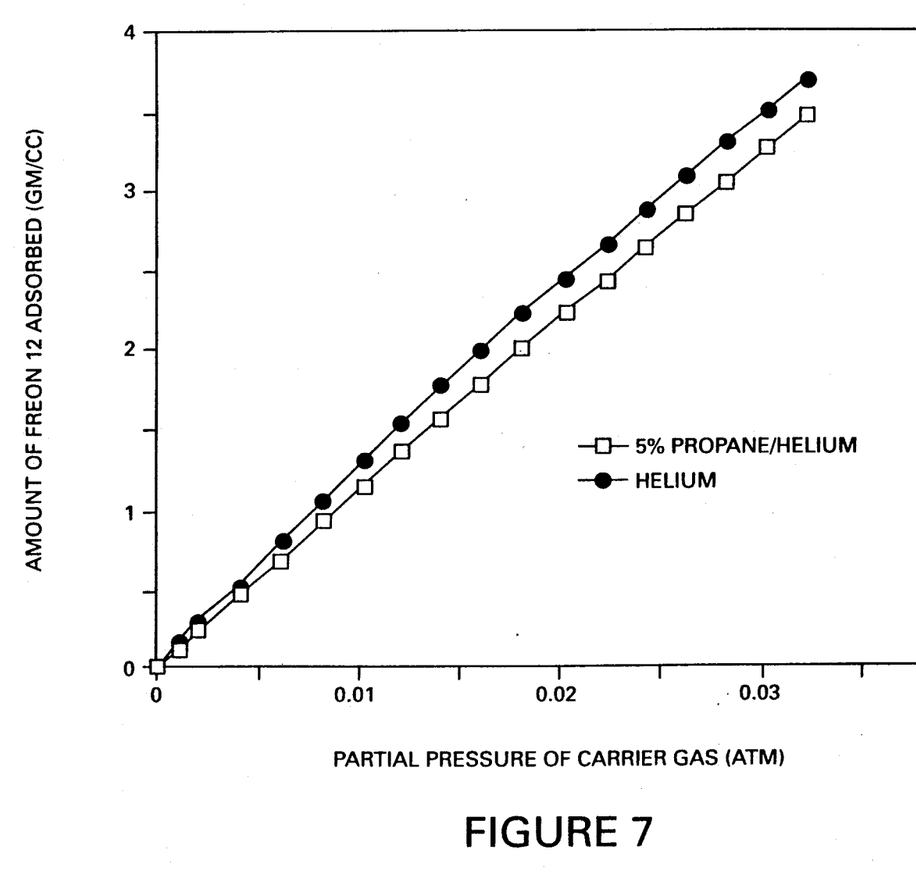
FIG. 7 illustrates an adsorption isotherms for Freon®12 on coconut charcoal.

This experiment was performed twice, first with pure helium and then with 5% propane in helium. The isotherms are given in FIG. 7. Note the relative reduction of the isotherm with 5% propane in helium compared to no propane or pure helium. These results indicate that the degree of adsorption of Freon® 12 onto coconut charcoal is reduced in the presence of only 5% propane. Experimentally, a propane concentration of 5% in helium was the highest concentration that the thermal conductivity detector could tolerate. As a result, pure propane could not be examined. However, the results obtained in Example 6 demonstrate that the propane effect is linear with propane concentration. Accordingly, the adsorption isotherm of pure propane will be reduced by a factor of 20.

This provides another quantitative method of demonstrating the effect of hydrocarbon gases on the adsorption of halocarbons carbonaceous adsorbents.

EXAMPLE 10

Figure 8:
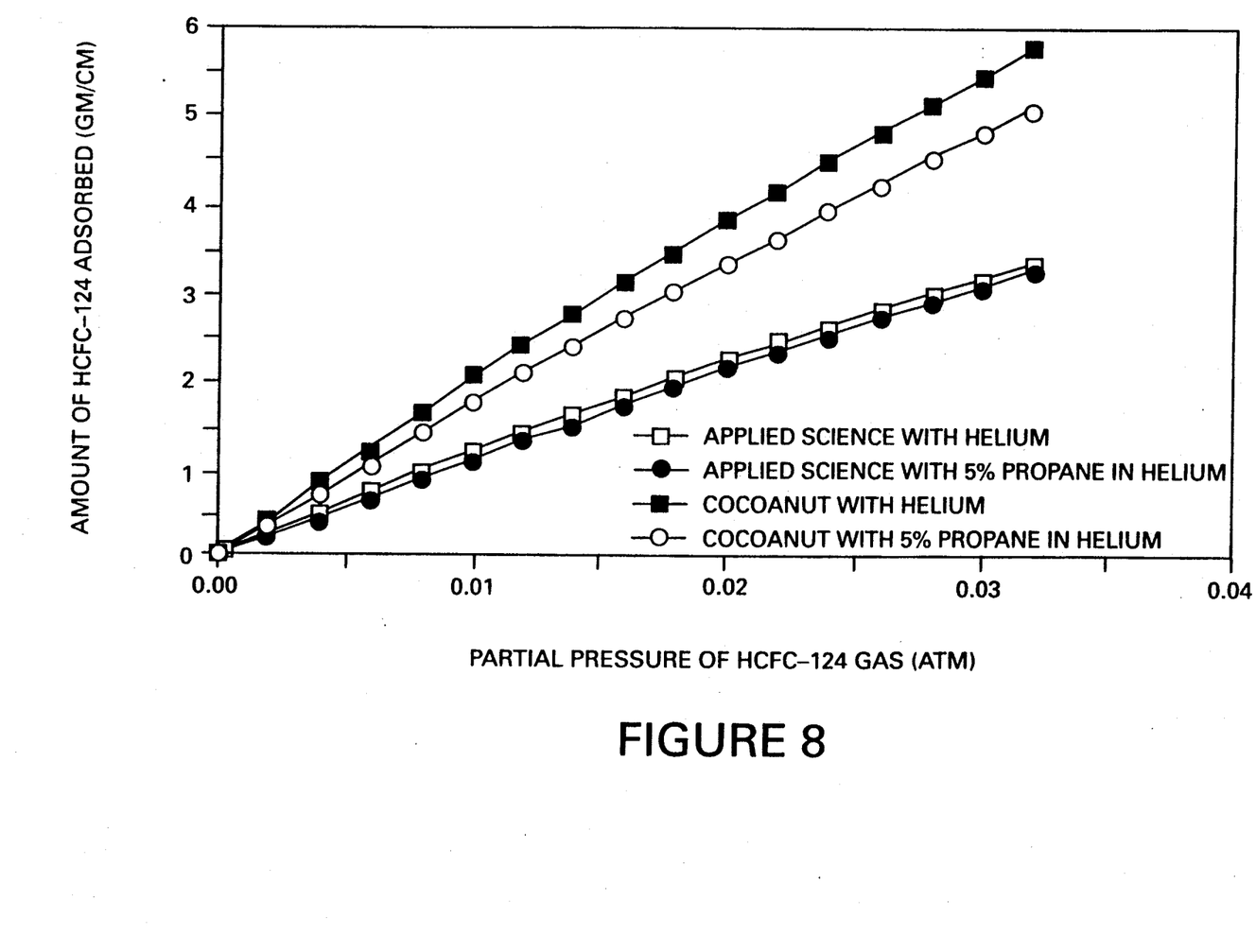
FIG. 8 shows adsorption isotherms for HCFC-124 on coconut and Applied Science charcoals.

The effect of hydrocarbon gases on halocarbon recovery from carbonaceous adsorbents was also demonstrated for another halocarbon, HCFC-124 or 2-chloro-1,1,1,2 tetrafluoroethane. Coconut and Pittsburgh charcoals were prepared. The adsorption isotherms for HCFC-124 on each charcoal were determined by gas chromatography. The results are shown in FIG. 8. As in Example 9. the adsorption isotherms for HCFC-124 are reduced in the presence of 5% propane on both coconut and Pittsburgh charcoals, although to differing degrees. As in Example 10, if pure propane had been used, the reduction of the adsorption isotherm would have increased by a factor of 20.

These examples show the effect of using hydrocarbon gas on the adsorptivity of halocarbons onto carbonaceous adsorbents. These examples also demonstrate that propane reduces the adsorption ability of the carbonaceous adsorbent.

Thus, while there have been disclosed what are presently believed to be the preferred embodiments of the present invention. Other and further manifestations of the invention will become apparent to those skilled in the art, and it is intended to claim all such changes and modifications as come within the true scope of the present invention.

We claim:

1. A process for regeneration of a halocarbon-bearing carbon adsorbent comprising contacting said adsorbent with a hydrocarbon gas stream from the group consisting of propane, butane, pentane, natural gas and mixtures thereof at about room temperature and atmospheric pressure whereby said halocarbons, which have been adsorbed on the carbon adsorbent, are displaced by said hydrocarbons.

2. A process according to claim 1 wherein said carbon adsorbent is selected from the group consisting of bone, char, coke, charcoal and activated carbon.

3. A process according to claim 1 wherein said halocarbons are perfluorocarbons in trace amounts.

4. A process according to claim 1, wherein said halocarbons are selected from the group consisting of perfluoro-dimethylcyclobutane, perfluoro-methylcyclopentane, perfluoro-methylcyclohexane, perfluoro-1,2 dimethylcyclohexane, perfluoro-1,3 dimethylcyclohexane, perfluoro-1,4 dimethylcyclohexane, perfluoroethylcyclohexane, perfluoro-ortho(trans)-dimethylcyclohexane, perfluoro-meta(cis)-dimethylcyclohexane, perfluoro-para(trans)-dimethylcyclohexane, perfluoro-1-trimethylcyclohexane, perfluoro-2-trimethylcyclohexane, trichlorofluoromethane, dichlorodifluoromethane, dichlorofluoromethane, chlorodifluoromethane and chlorotetrafluoroethane.

5. A process according to claim 1, wherein said hydrocarbon eluting stream is passed through said adsorbent at a flow rate from about 4.0 cc/min to about 20 cc/min. for a period from about 5 minutes to about 30 minutes.

6. A process of claim 1, wherein said carbon adsorbed is pelletized, granular or briquetted.

7. A process according to claim 1, wherein said regeneration is substantially complete.

* * * * *